United States Patent [19]

Meyer

[11] Patent Number: 5,464,614
[45] Date of Patent: Nov. 7, 1995

[54] STABILIZED SUPEROXIDE DISMUTASE (SOD) COMPOSITION

[75] Inventor: Reiner Meyer, Maria Enzersdorf, Austria

[73] Assignee: Boehringer Ingelheim International GmbH, Germany

[21] Appl. No.: 152,015

[22] Filed: Nov. 15, 1993

[30] Foreign Application Priority Data

Nov. 27, 1992 [DE] Germany .......................... 42 39 877.0

[51] Int. Cl.⁶ .................................................. A61K 38/44
[52] U.S. Cl. .......................... 424/94.3; 424/94.4; 424/94.1
[58] Field of Search .................................. 424/94.1, 94.3, 424/94.4

[56] References Cited

U.S. PATENT DOCUMENTS

| | | | |
|---|---|---|---|
| 4,346,174 | 8/1982 | Yasuda et al. | 435/189 |
| 5,024,998 | 6/1991 | Bodor | 424/94.1 |
| 5,246,847 | 9/1993 | Hartman et al. | 435/189 |
| 5,260,204 | 11/1993 | Heckl et al. | 435/189 |
| 5,298,410 | 3/1994 | Phillips et al. | 435/188 |

FOREIGN PATENT DOCUMENTS

| | | |
|---|---|---|
| 891160 | 3/1982 | Belgium . |
| 0080879 | 6/1983 | European Pat. Off. . |
| 0091258 | 10/1983 | European Pat. Off. . |
| 0123291 | 10/1984 | European Pat. Off. . |
| 0142345 | 5/1985 | European Pat. Off. . |
| 0162332 | 11/1985 | European Pat. Off. . |
| 0180964 | 5/1986 | European Pat. Off. . |
| 0188053 | 7/1986 | European Pat. Off. . |
| 0210761 | 2/1987 | European Pat. Off. . |
| 0218480 | 4/1987 | European Pat. Off. . |
| 0231132 | 8/1987 | European Pat. Off. . |
| 0284105 | 9/1988 | European Pat. Off. . |
| 0292321 | 11/1988 | European Pat. Off. . |
| 0355348 | 2/1990 | European Pat. Off. . |
| 0359617 | 3/1990 | European Pat. Off. . |
| 0483113 | 4/1992 | European Pat. Off. . |
| 0492447 | 7/1992 | European Pat. Off. . |
| 1304882 | 12/1989 | Japan . |
| 2183658 | 6/1987 | United Kingdom . |
| WO85/01503 | 4/1985 | WIPO . |
| WO87/01387 | 3/1987 | WIPO . |
| WO88/09674 | 12/1988 | WIPO . |
| WO89/12677 | 12/1989 | WIPO . |
| WO90/01260 | 2/1990 | WIPO . |
| WO90/03784 | 4/1990 | WIPO . |
| WO91/06634 | 5/1991 | WIPO . |

OTHER PUBLICATIONS

European Search Report for Application No. 93118801.5 dated Oct. 4, 1994 (3 pages).

"Anti–Inflammatory Compositions Containing Orgotein–With Excess Mannitol as Potentiator", BE–891160, available in Derwent World Patent Index, STN (Abstract).

Barra et al., "The Primary Structure of Human Liver Manganese Superoxide Dismutase", *J. Biol. Chem.* 259:12595–12601 (Oct. 25, 1984).

Brewster et al., "Use of 2–Hydroxypropyl–β–cyclodextrin as a Solubilizing and Stabilizing Excipient for Protein Drugs", *Pharm. Res.* 8:792–795 (1991).

Gorecki et al., "Recombinant Human Superoxide Dismutases: Production and Potential Therapeutical Uses", *Free Rad. Res. Comms.* 12–13:401–410 (1991).

Hartz & Deutsch, "Subunit Structure of Human Superoxide Dismutase", *J. Biol. Chem.* 247:7043–7050 (Nov. 10, 1972).

Hora et al., "Lyophilized Formulations of Recombinant Tumor Necrosis Factor", *Pharm. Res.* 9:33–36 (1992).

Jabusch et al., "Some Sulfhydryl Properties and Primary Structure of Human Erythrocyte Superoxide Dismutase", *Biochem.* 19:2310–2316 (1980).

Lee & Fennema, "Ability of Cyclodextrins to Inhibit Aggregation of β–Casein", *J. Agric. Food Chem.* 39:17–21 (1991).

Marres et al., "Nucleotide sequence analysis of the nuclear gene coding for manganese superoxide dismutase of yeast mitochondria, a gene previously assumed to code for the Rieske iron–sulfur protein", *Eur. J. Biochem.* 147:153–161 (1985).

McCord & Fridovich, "Superoxide Dismatase: An Enzymic Function for Erythrocuprein (humocuprein)", *J. Biol. Chem.* 244:6049–6055 (Nov. 25, 1969).

McCord et al., "A Manganese–Containing Superoxide Dismutase from Human Liver", *Superoxide and Superoxide Dismutases*, Academic Press, London, pp. 129–138 (1977).

Nimrod et al., "Recombinant Human Manganese Superoxide Dismutase (r–hMnSOD) is a Potent Anti–Inflammatory Agent", *Med. Biochem. & Chem. Aspects of Free Raficals*, pp. 743–746 (1989).

Pitha et al., "Molecular Encapsulation of Drugs by Cyclodextrins and Congeners", *Controlled Drug Delivery* (Bruck, S. D., ed.) vol. I, CRC Press, Boca Raton, Fla., pp. 125–148 (1983).

*Primary Examiner*—Marian C. Knode
*Assistant Examiner*—Jean C. Witz
*Attorney, Agent, or Firm*—Sterne, Kessler, Goldstein & Fox

[57] ABSTRACT

A stabilized superoxide dismutase (SOD) composition contains as additives cyclodextrin, preferably hydroxypropyl-β-cyclodextrin, and either a sugar or a sugar alcohol, preferably mannitol.

Freeze-dried formulations with the composition according to the invention yield clear solutions with a high enzymatic activity on resolvation.

6 Claims, No Drawings

STABILIZED SUPEROXIDE DISMUTASE (SOD) COMPOSITION

FIELD OF THE INVENTION

The present invention is in the field of medicinal chemistry. In particular, the invention relates to stabilized pharmaceutical compositions comprising a superoxide dismutase.

BACKGROUND OF THE INVENTION

It is known that, as a consequence of various biochemical processes in biological systems (e.g. redox processes in the respiratory chain, oxidations in the cytoplasm), $O_2$ radicals are continuously formed which are highly cytotoxic and which may lead to tissue damage. In pathological situations, e.g. in the course of rheumatic disorders, it is believed that degradation of collagen and synovial fluid is caused by such radicals (Pasquier, C. et al., *Inflammation* 8:27–32, (1984)).

Eukaryotic cells contain primarily two forms of superoxide dismutases (SOD), one of which occurs predominantly in the cytosol (Cu/Zn-SOD) and the other in the mitochondria (Mn-SOD). In liver mitochondria, it has been found that the Mn-enzyme is located in the matrix enclosing the inner membrane. Mn-SOD has also been detected in the cytosol of liver cells (McCord J. M. et al. In: *Superoxide and Superoxide Dismutases* (A. M. Michelson, J. M. McCord, I. Fridovich, eds.) Academic Press, N.Y., 129–138, (1977)).

In prokaryotes, there is an Fe-SOD in addition to a MnSOD. Fe-SOD has also been detected in algae and protozoa and in some plant species (Bridges, S. M., Salin, M. L., *Plant Physiol.* 68:275–278 (1981)). These highly active enzymes catalyze the disportionation $O_2+O_2+2H^+ \rightarrow H_2O_2+O_2$. By this dismutation of the superoxide radicals, the concentration of the radicals and hence cell damage is prevented. Apart from the endoplasmic reticulum of the liver, the mitochondrial membranes are regarded as one of the most important sites of $O_2$ production in animal cells. Thus, it is not surprising that mitochondria have their own special SOD (Mn-SOD).

The structural gene of a prokaryotic Mn-SOD (*E. coli*) has been cloned and the chromosomal sodA-gene has been located (Touati, D., *J. Bact.* 155: 1078–1087 (1983)).

The 699 bp long nucleotide sequence of a mitochondrial yeast Mn-SOD has been clarified and the primary structure both Of the precursor and of the mature protein have been derived therefrom—with molecular weights of 26123 Da for the precursor and 23059 Da for the mature. protein (Marres, C. A. M. et al., *Eur. J. Biochem.* 147:153–161 (1985)). Thus, the Mn and Cu/ZnSOD (MW=14893, EP-A-138111) differ significantly in their molecular weights.

The complete amino acid sequence of Mn-SOD from human liver has been published by Barra D., et al. *J. Biol. Chem.* 259:12595–12601 (1984). According to Barra et al., hMn-SOD consists of 196 amino acids. Human Cu/Zn-SOD from erythrocytes, on the other hand, consists of 153 amino acids (Jabusch, J. R., et. al. *Biochemistry* 19:2310–2316, (1980) and exhibits no sequence homologies to hMn-SOD (Barra, D. et al., see above).

The preparation of the SOD, particularly by the methods of DNA recombination, is well known in the art and has been frequently described. For example, the human Cu/Zn-SOD may be prepared according to EP-A 0 138 111, EP-A 0 180 964, WO 85/01503 and WO 91/06634. Human Mn-SOD can be obtained using the method described in EP-A 0 282 899. The preparation of EC-SOD is described in EP-A 0 236 385 and EP-A 0 492 447. Fe-SOD may be prepared according to EP-A 218 480 and vegetable SODs may be prepared according to EP-A 0 359 617, EP-A 0 356 061 and WO 90/01260. An Mn-SOD frown Serratia is disclosed in EP-A 0 210 761.

The preparation and recovery of SOD by Conventional methods, e.g. by extraction from cells and/or tissues of animal or human origin and subsequent purification, e.g. by chromatographic separation, has also been described elsewhere (e.g. EP-A 0 188 053, DE-OS 3124 228). In addition, chemically modified derivatives of SOD or SOD-analogs are well known and are disclosed for example in EP-A 0 292 321, EPA 0 483 113 and WO 89/012677.

Numerous attempts have been made to stabilize biologically active proteins by the addition of various substances and mixtures. For example, it is proposed according to EP-A 0 142 345 to stabilize interferons by adding a protease inhibitor; alternatively, sugar alcohols are described for achieving a stabilizing effect (EPA 0 080 879). In addition to these stabilizers, human serum albumin (EP-A 0 162 332), dextrans, dextrins and other saccharides (EP-A 0 123 291), albumin with sugar or sugar alcohols (EPA 0 231 132), gelatine (EP-A 0 091 258) or certain buffer systems (WO 88/09674) have also been disclosed as stabilizing agents in biologically active proteins (interferons, TNF, IL-2).

WO 90/03784 describes the use of β- and γ-cyclodextrin derivatives, particularly hydroxypropyl-β-cyclodextrin (HPBCD) for stabilizing various biologically active proteins. This patent application describes stabilization or solubilization or the prevention of aggregation with HPBCD, in particular, explicitly for interleukin-2 (IL-2), tumor necrosis factor (TNF), macrophage colony stimulating factor (m-CSF), insulin and human growth hormone (HGH). See also, Brewster, M. E. et al., *Pharm. Res* 8:792–795 (1991).

It is known from Lee, M. and Fennema O. R., *J. Agric. Food Chem.* 39:17–21 (1991), that cyclodextrins prevent the clumping of β-caseine.

The publication by Hora M. S. et al., *Pharm. Res.* 9:33–36 (1992), discloses how the formation of soluble dimers of tumor necrosis factor (TNF) in lyophilized form can be prevented if before the lyophilization, mannitol is added to the TNF together with an amorphous component (dextran, saccharose, trehalose or 2- hydroxypropyl-β-cyclodextrin).

SUMMARY OF THE INVENTION

In view of the potential clinical importance of SODs, there is a need for stabilized formulations of these proteins. This is particularly true of lyophilized SOD preparations which, according to the invention, yield clear solutions when resolvated. Attempts to do this by adding mannitol, saccharose, Tween 20®, Tween 80® or serum albumin have failed.

In particular, the invention relates to a composition which is soluble in aqueous solution, comprising superoxide dismutase, cyclodextrin and a sugar or a sugar alcohol.

The invention also relates to a process foe preparing a composition comprising superoxide dismutase which is soluble in aqueous solution, comprising forming an aqueous solution of a :superoxide dismutase, a cyclodextrin, and a sugar or a sugar alcohol. Preferably, the solution is lyophilized.

The invention also relates to a pharmaceutical composition, comprising superoxide dismutase, cyclodextrin and a sugar or .a sugar alcohol.

The invention also relates to the use of the compositions of the invention for preparing a medicament for the treatment or prophylaxis of a disease in a mammal.

The invention also relates to the use of superoxide dismutase, hydroxypropyl-β-cyclodextrin and mannitol for preparing a medicament for the treatment or prophylaxis of a disease in a mammal

DETAILED DESCRIPTION OF THE INVENTION

The invention relates to stabilized superoxide dismutase (SOD) compositions in which the constituents SOD, a cyclodextrin, a sugar and/or a sugar alcohol are present in combination; correspondingly stabilized pharmaceutical preparations with SOD as the pharmacologically active agent; the use of the individual components for preparing such compositions and preparations; a process for preparing compositions stabilized in this way and pharmaceutical preparations; and the use of said combinations for treating diseases and for preventative treatment in mammals and in humans. Such diseases include any disease or condition which may benefit from the administration of SOD. Such diseases and conditions include, but are not limited to, inflammation, lung fibrosis, injury caused by reperfusion following ischemia, bronchial pulmonary dysplasia, fibrosis following radiation treatment, and to increase the survival time of excised isolated organs. See, EP 0 284 105. The compositions may also be used to treat hyperoxia of the lung.

The SODs which may be used according to the invention include all the known derivatives and analogs of SODs having a known biological or enzymatic spectrum of activity. See, for example, McCord J. M. et al. In: *Superoxide and Superoxide Dismutases* (A. M. Michelson, J. M. McCord, I. Fridovich, eds.) Academic Press, N.Y., 129–1382, (1977); Bridges, S. M., Salin, M. L., *Plant Physiol.* 68:275–278 (1981) (Fe-SOD); Touati, D., *J. Bact.* 155:1078–1087 (1983) (Mn-SOD from *E. coli*); Marres, C. A. M. et al., *Eur. J. Biochem.* 147:153–161 (1985) (mitochondrial yeast Mn-SOD); EP-A-138111 (Mn and Cu/ZnSOD); Barra D., et al. *J. Biol. Chem.* 259:12595–12601 (1984) (Mn-SOD from human liver); Jabusch, J. R., et. al. *Biochemistry* 19:2310–2316, (1980) (human Cu/ZnoSOD from erythrocytes); EP-A 0 138 111, EP-A 0 180 964, WO 85/01503 and WO 91/06634 (Cu/Zn-SOD); EP-A 0 282 899 (human Mn-SOD); EP-A 0 236 385 and EP-A 0 492 447 (EC-SOD); EP-A 218 480 (Fe-SOD); EP-A 0 359 617, EP-A 0 356 061 and WO 90/01260 (vegetable SODs); and EP-A 0 210 761 (Mn-SOD from Serratia);

The cyclodextrins which may be used according to the invention are cyclic oligosaccharides or cyclic polymers the ring systems of which consist of six, seven or eight α-1,4-linked glucose units, and are referred to as α, β- or γ-cyclodextrins, according to the number of respective monomers. It is known that the cyclodextrins form inclusion complexes with various biomolecules, such as fatty acids or amino acids, and are able to include the latter up to saturation point. Of the cyclodextrins, those used are preferred include the β-cyclodextrins and chemically modified derivatives thereof, which may be used to prepare stable, aqueous protein solutions and to test the toxicity thereof. Out of the very large amount of literature published up till now concerned with the preparation and use of cyclodextrins, particularly the β-cyclodextrins, the following publications are mentioned only by way of example: Manning, M. et al., *Pharm. Res.* 6:1903;1918, (1989); Yoshida, A. et al., *Int. J. Pharm.* 461:217–222, (1988); Brewster, M. et al., *Int. J. Pharm.* 59:231–243 (1980); Pitha, J. et al., *Int. J. Pharm.* 29:73–82 (1986); Pitha, J. & Pitha J., *J. Pharm. Sci.* 74:987–990, (1985); Brewster, M. et al., *J. Parent. Sci. Technol.* 43:231–240 (1978). In particular, Pitha J. & Pitha, J. (1986), loc. cit. describe the preparation of hydroxypropyl-β-cyclodextrin (HPBCD). They have reported that the use of HPBCD improves the water solubility of all kinds of active substances and Biological macromolecules. Regarding the use of cyclodextrins in pharmaceuticals reference is made to the summarizing article by Pitha, J. et al., in: Controlled Drug Delivery [Bruck, S. D., ed.] Vol. I, CRC Press, Boca Raton, Fla., 125–148, 1983, or to Uekama, K., et al., in: CRC Critical Reviews in Therapeutic Drug Carrier Systems, Vol.3 (1), 1–40, 1987; or to Uekama, K., in: Topics in Pharmaceutical Sciences 1987 [Breimer, D.D. and Speiser, p., eds.] Elsevier Science Publishers B.V. (Biomedical Division), 181–194, 1987. The use of 2-hydroxypropyl-/β-cyclodextrin, in particular, for solubilizing and stabilizing various biologically active proteins is described more fully by Brewster, M. E. et al., *Pharm. Res.* 8:792–795 ( 1991 ).

The sugars which may be used in the practice of the invention are the monosaccharides, particularly the aldohexoses, ketohexoses and the derivatives thereof and optical isomers thereof and the disaccharides, such as D(+)-glucose, D(+)-mannose, D(+)-galactose, D(−)fructose, D(+)-sorbose, saccharose, lactose and maltose.

The sugar alcohols which-may be used in the practice of the invention include the monosaccharides reduced to the corresponding polyhydric alcohols, e.g. those which may be derived from the above-mentioned monosaccharides, mannitol or D-mannitol being particularly preferred.

A particular problem of the superoxide dismutases is that the enzymatically active forms are oligomers consisting of non-covalently associated subunits; in the case of Cu/Zn-SOD a dimer (Hartz & Deutsch, *J. Biol. Chem.* 247:7043–50 (1972)), in the case of Mn-SOD a tetramer(McCord et al. (eds.), Superoxide and Superoxide Dismutases, Academic Press, London (1977), p. 129–38). Stabilizing additives should prevent the formation of insoluble high molecular aggregates but not prevent the aggregation into the enzymatically active oligomer.

Prior to the present invention, there was no process available for formulating an enzyme consisting of a number of noncovalently aggregated subunits, such as superoxide dismutase, in such a way as to avoid the formation of insoluble aggregates, without impairing the association of the subunits and hence the enzymatic activity. A particular problem is the preparation of highly concentrated solutions (10–60 mg/ml SOD).

Surprisingly, it has been found that the combined addition of a cyclodextrin, e.g. HPBCD, and one or more sugars or sugar alcohols before lyophilization of SOD solutions can prevent the formation of insoluble high molecular aggregates without preventing the desired aggregation into the enzymatically active oligomer. The combination! of HPBCD with mannitol proved particularly suitable. The invention is related in part to this discovery.

The formulations of superoxide dismutase according to the invention are conveniently produced in the form of a freeze-dried preparation. Such lyophilisates, after resolvating, yield clear solutions with a high enzymatic activity.

The solutions intended for freeze-drying may contain superoxide dismutase in concentrations of from 0.1 to 60 mg/ml. Concentration of ≧5 mg/ml, more especially ≧10 mg/ml, are preferred. Preferably, these solutions contain hydroxypropyl-β-cyclodextrin in an amount of 0.5–20% (weight/volume), preferably 1–11%, more especially 1–6%, and mannitol in an amount of from 0.5–10 %, preferably 1–5 % (weight/volume).

Having now generally described this invention, the same will be understood by reference to an example Which is provided herein for purposes of illustration only and is not intending to be limited unless otherwise specified. The entire text of all applications, patents and publications, if any, cited above and below are hereby incorporated by reference in their entirety.

EXAMPLE

Experimental Process For Preparing Lyophilisates And Resolvated Products

Mn-SOD was prepared according to EP-A 282 899. Hydroxypropyl-β-cyclodextrin was obtained from ICN Biomedicals GmbH, Meckenheim, FRG, and D-mannitol was obtained from Serva Feinbbchemica GmbH & Co., Heidelberg, FRG.

The SOD-containing concentrate (20–40 mg/ml of Mn-SOD, 150 mM sodium chloride, 10 mM sodium phosphate, pH 7.2) was dialyzed against the buffer which was to be used in the corresponding formulation (see below). After 2 hours in each case the buffer solution was changed 3 times. The exclusion limit of the dialysis tube was for molecular weights $\geq 10,000$ Da.

However, dialysis was not necessary if the corresponding formulation was to contain 10 mM sodium phosphate and sodium chloride in the range from 75–150 mM, since the concentration of Mn-SOD in the concentrate was high enough to achieve the desired final concentration of the additives after the additive solution had been mixed in.

A Solution with additives was formed in a buffer solution so that, after the Mn-SOD-containing solution had been mixed with the buffer solution containing the additives, the desired final concentrations of all the substances were obtained.

The formulation thus produced was transferred into ampoules in amounts of 1.0 ml. These filled ampoules were lyophilized (frozen to −40° C., kept at −40° C. for 2 hours, subjected to main drying at −30° C. and 0.02 mbar until the product ,temperature was equal to the shelf temperature, further drying at 0° C. for 4 hours and at +20° C. for 2 hours; freeze-drying equipment made by Edwards/Kniese, Lyofex 0.4).

After lyophilization, the ampoules were sealed with stoppers and stored in a refrigerator, at ambient temperature and at 40° C. in the dark. The entire manufacturing process was carried out under sterile conditions. After certain time intervals (up to a maximum of ½ year) the lyophilisates were redissolved with water and analyzed. Routine analysis was carried out on the nature of the lyo-cake, the characteristics of the resolvated product, the resolvated product itself, the specific Mn-SOD activity (McCord and Fridovich, *J. Biol. Chem.* 244:6049 (1969)) and on any breakdown products and aggregates, using polyacrylamide gel electrophoresis (Laemmli, *Nature* 227:680–5 (1970)).

Table 1 shows a number of formulations prepared according to this method. The additives tested were: sodium phosphate buffer (Na-phosphate), sodium phosphate-sodium citrate buffer (phos-citrate), mannitol, sodium chloride (NaCl), Tween 80®, cysteine, saccharose (sucrose) and hydroxypropyl-β-cyclodextrin (HPBCD). After 1–2 weeks' storage, the first cloudiness could be detected in those formulations which did not contain the combination of HPBCD and mannitol, stored at 21° and at 40° C. The formulations containing the combination of HPBCD and mannitol showed no cloudy resolvated products even at 40° C. after 7 months' storage.

In addition to the formulations shown in Table 1 which were prepared with an Mn-SOD concentration of 10 mg/ml, formulations were prepared from solutions containing 0.1, 1.0 and 20 mg/ml of Mn-SOD.

The last 3 columns show the evaluations Of the observations which showed the clearest difference between the formulations: cloudiness of the resolvated products after storing the lyophilisates at various temperatures (5 ° C., 21° C., 40° C.).

Having now fully described this invention; it will be understood by those of ordinary skill in the art that it can be performed within a wide equivalent range of modes of operation as well as other parameters without affecting the scope of the invention or any embodiment thereof.

TABLE 1

Resolvated product properties of various MnSOD preparations (lyophilysates)

| [MnSOD] (mg/ml) | [Mannitol][1] (mM) | [NaCl] (%) | [HPBCD] (%) | Buffer | Cloudiness[2] 5° C. | 21° C. | 40° C. |
|---|---|---|---|---|---|---|---|
| 10 | | | 5 | Phos-Citrate 10 mM pH 7.2 | 0 | 0 | ++ |
| 10 | 2 | | 6 | Phos-Citrate 10 mM pH 7.2 | 0 | 0 | 0 |
| 10 | 1 | | 11 | Phos-Citrate 10 mM pH 7.2 | 0 | 0 | 0 |
| 10 | | 61 | 6 | Phos-Citrate 10 mM pH 7.2 | 0 | + | ++ |
| 10 | | 34 | 11 | Phos-Citrate 10 mM pH 7.2 | 0 | 0 | ++ |
| 10 | 2 | | 6 | Na-Phosphate 10 mM pH 7.2 | 0 | 0 | 0 |
| 10 | | 61 | 6 | Na-Phosphate 10 mM pH 7.2 | 0 | ++ | +++ |
| 10 | 4.5 | | 1 | Na-Phosphate 10 mM pH 7.2 | 0 | 0 | 0 |
| 10 | | 150 | | Na-Phosphate 10 mM pH 7.2 | +++ | | |
| 10 | 5 | | | Na-Phosphate 10 mM pH 7.2 | +++ | +++ | +++ |
| 10 | Sucrose (0.3%) | 8.6 | | Na-Phosphate 0.5 mM pH 7.2 | + | | |

[1] or the additive specified
[2] cloudiness: the dry ampoules stored at three temperatures (5° C., 21° C., 40° C.) were measured by eye ¼ of an hour after resolvation, the degree of cloudiness being categorized in one of the following 4 categories:
0 = clear solution; + = few particles and/or very slightly cloudy; ++ = numerous particles and/or plainly cloudy; +++ = extremely cloudy or flakey

What is claimed is:

1. A water soluble composition comprising 0.1–10 mg/ml manganese superoxide dismutase, 1–11% (weight/volume) hydroxypropyl-β-cyclodextrin, and 1.0–4.5% (weight/volume) mannitol.

2. A pharmaceutical composition comprising 0.1–10 mg/ml manganese superoxide dismutase, 1–11% (weight/volume) hydroxypropyl-β-cyclodextrin, and 1.0–4.5% (weight/volume) mannitol and a pharmaceutically acceptable carrier.

3. A process for preparing a composition comprising water soluble manganese superoxide, comprising forming an aqueous solution of 0.1–10 mg/ml manganese superoxide dismutase, 1–11% (weight/volume) hydroxypropyl-β-cyclodextrin, and 1.0–4.5% (weight/volume) mannitol.

4. The process of claim 3 wherein the aqueous solution has been lyophilized.

5. A lyophilized composition obtained by the process of forming an aqueous solution of 0.1–10 mg/ml manganese superoxide dismutase, 1–11% (weight/volume) hydroxypropyl-β-cyclodextrin, and 1.0–4.5% (weight/volume) mannitol and lyophilizing said aqueous solution.

6. A lyophilized pharmaceutical composition obtained by the process of forming an aqueous solution of 0.1–10 mg/ml manganese superoxide dismutase, 1–11% (weight/volume) hydroxypropyl-β-cyclodextrin and 10–4.5% (weight/volume) mannitol in a pharmaceutically acceptable carrier and lyophilizing said aqueous solution.

* * * * *

UNITED STATES PATENT AND TRADEMARK OFFICE
CERTIFICATE OF CORRECTION

PATENT NO. : 5,464,614

DATED : November 7, 1995

INVENTOR(S) : MEYER

It is certified that error appears in the above-indentified patent and that said Letters Patent is hereby corrected as shown below:

On the title page item [30],

Under the heading "Foreign Application Priority Data", before "42 39 877.0", insert --P--.

Under the heading "OTHER PUBLICATIONS", in the citation to McCord and Fridovich, line 2 delete "(humocuprein)" and insert therefor --(hemocuprein)--.

Under the heading "OTHER PUBLICATIONS", in the citation to Nimrod et al., line 3, delete "rajicals" and insert therefor --radicals--.

Column 1, line 35, delete "$O_2 + O_2$" and insert therefor --$O_2^{\cdot-} + O_2^{\cdot-}$--;
    line 40, delete "$O_2$" and insert therefor --$O_2^{\cdot-}$--;
    line 49, delete "Of" and insert therefor --of--;
    line 51, delete "mature." and insert therefor, --mature--;
    line 56, delete "Barra D., et al." and insert therefor --Barra, D. et al.,--;
    line 60, "after "J.R.", delete ", et al." and insert therefor "et al.,";
    line 61, after "(1980)", insert --)--.

Column 2, line 6, delete "frown", and insert therefor --from--;
    line 7, delete "Conventional" and insert therefor --conventional--;
    line 40, after "Hora", insert --,--;
    line 59, delete "foe" and insert therefor --for--;
    line 62, delete ":superoxide" and insert therefor --superoxide--;
    line 67, delete ".a" and insert therefor --a--.

UNITED STATES PATENT AND TRADEMARK OFFICE
CERTIFICATE OF CORRECTION

PATENT NO. : 5,464,614

DATED : November 7, 1995

INVENTOR(S) : MEYER

It is certified that error appears in the above-indentified patent and that said Letters Patent is hereby corrected as shown below:

Column 3, line 7, after "mammal", insert --.--;
      line 29, delete "See," and insert therefor --See--;
      line 35, after "McCord," insert --,--;
      line 35, after "et al.", insert ",";
      line 35, delete "In:" and insert therefor --in:--;
      line 37, delete "1382" and insert therefor --138--;
      line 42, delete "Barra D., et al." and insert therefor --Barra, D. et al.,--;
      line 44, after "Jabusch, J. R.", delete ", et. al." and insert therefor --et al.,---,
      line 45, delete "Cu/ZnoSOD" and insert therefor --Cu/Zn-SOD--;
      line 55, delete "$\alpha$," and insert therefor --$\alpha$-,--.

Column 4, line 1, delete "1903;1918" and insert therefor --1903-1918--;
      line 10, delete "Biological" and insert therefor --biological--;
      line 20, delete "/$\beta$" and insert therefor --$\beta$--;
      line 27, delete "D(-)fructose" and insert therefor --D(-)-fructose--;
      line 57, delete "combination!" and insert therefor --combination--;
      line 67, delete "$\geq 5$" and insert therefor --$\geq 5$--;
      line 67, delete "$\geq 10$" and insert thereforfor --$\geq 10$--.

UNITED STATES PATENT AND TRADEMARK OFFICE
CERTIFICATE OF CORRECTION

PATENT NO. : 5,464,614

DATED : November 7, 1995

Page 3 of 4

INVENTOR(S) : MEYER

It is certified that error appears in the above-indentified patent and that said Letters Patent is hereby corrected as shown below:

Column 5, line 7, delete "Which" and insert therefor --which--;
    line 9, delete "intending" and insert therefor --intended--;
    line 22, delete "Feinbbchemica" and insert therefor --Feinbiochemica--;
    line 30, delete "$\geq$" and insert therefor --$\geq$--;
    line 37, delete "Solution" and insert therefor --solution--;
    last line, delete both occurrences of "C." and insert both times therefor --C--.

Column 6, line 1, delete "C." and insert therefor --C--;
    line 2, delete ",temperature" and insert therefor --temperature--;
    line 3, delete both occurrences of "C." and insert both times therefor --C--;
    line 8, delete "C." and insert therefor --C.--;
    line 30, delete "C." and insert therefor --C--;
    line 35, delete "Of" and insert therefor --of--;
    lines 39 and 40, delete all three occurrences of "C." and insert all three times therefor --C--

UNITED STATES PATENT AND TRADEMARK OFFICE
CERTIFICATE OF CORRECTION

PATENT NO. : 5,464,614

DATED : November 7, 1995

INVENTOR(S) :
MEYER

It is certified that error appears in the above-indentified patent and that said Letters Patent is hereby corrected as shown below:

Table 1, column 2, line 3, under the heading "[Mannitol]$^1$", delete "(mM)" and insert therefor --%--
    column 3, line 3, under the heading "[NaCl]", delete "%" and insert therefor --(mM)--;
    columns 6-8, line 3, under the heading "Cloudiness$^2$", delete all three occurrences of "C." and insert all three times therefor --C--;
    four lines from the bottom, delete all three occurrences of "C." and insert all three times therefor --C--.

Column 8, line 11, delete "10" and insert therefor --1.0--.

Signed and Sealed this

Thirtieth Day of April, 1996

Attest:

BRUCE LEHMAN

*Attesting Officer*          Commissioner of Patents and Trademarks